United States Patent
Wilkinson

(10) Patent No.: US 9,916,528 B2
(45) Date of Patent: Mar. 13, 2018

(54) APPARATUS AND METHOD TO DETERMINE A FROZEN STATE OF AN OBJECT AS A FUNCTION OF AN RFID TAG RECEPTIONPARAMETER

(71) Applicant: Wal-Mart Stores, Inc., Bentonville, AR (US)

(72) Inventor: Bruce W. Wilkinson, Rogers, AR (US)

(73) Assignee: Wal-Mart Stores, Inc., Bentonville, AR (US)

( * ) Notice: Subject to any disclaimer, the term of this patent is extended or adjusted under 35 U.S.C. 154(b) by 0 days.

(21) Appl. No.: 15/180,688

(22) Filed: Jun. 13, 2016

(65) Prior Publication Data
US 2016/0379023 A1 Dec. 29, 2016

Related U.S. Application Data

(60) Provisional application No. 62/185,480, filed on Jun. 26, 2015.

(51) Int. Cl.
*G06K 19/07* (2006.01)
*G01N 22/04* (2006.01)

(52) U.S. Cl.
CPC ......... *G06K 19/0717* (2013.01); *G01N 22/04* (2013.01)

(58) Field of Classification Search
CPC ........................... G06K 7/10366; G01N 22/04
USPC ........................................................ 340/10.1
See application file for complete search history.

(56) References Cited

U.S. PATENT DOCUMENTS

| | | | | |
|---|---|---|---|---|
| 4,507,530 A | * | 3/1985 | Smith | H05B 6/6447 219/703 |
| 5,005,005 A | * | 4/1991 | Brossia | B64D 15/20 250/573 |
| 7,446,662 B1 | * | 11/2008 | Somogyi | G06K 7/0095 340/10.41 |
| 2007/0188372 A1 | * | 8/2007 | Leath | G01K 11/006 342/26 R |

(Continued)

FOREIGN PATENT DOCUMENTS

| | | |
|---|---|---|
| EP | 2306129 | 4/2011 |
| WO | 2012140310 | 10/2012 |
| WO | 2014085638 | 6/2014 |

OTHER PUBLICATIONS

PCT; App. No. PCT/US2016/38901; International Search Report and Written Opinion dated Sep. 7, 2016.

*Primary Examiner* — Omar Casillashernandez
(74) *Attorney, Agent, or Firm* — Fitch, Even, Tabin & Flannery LLP

(57) ABSTRACT

A control circuit determines a reception parameter for an RFID tag that is attached to an object (such as an ice pack) and then determines a frozen state of the object as a function of that reception parameter. By one approach the RFID tag provides a transmission to support the aforementioned determinations, which transmission provides no data that explicitly represents temperature. The reception parameter can comprise, for example, an indication of received signal strength. So configured, a relatively higher indication of received signal strength can serve to determine that the object is and/or remains at least substantially frozen while a relatively lower indication of received signal strength can serve to determine that the object is not at least substantially frozen.

13 Claims, 2 Drawing Sheets

(56) References Cited

U.S. PATENT DOCUMENTS

| | | | |
|---|---|---|---|
| 2008/0218385 A1* | 9/2008 | Cook | B64D 15/20 340/962 |
| 2010/0079288 A1 | 4/2010 | Collins | |
| 2012/0256806 A1* | 10/2012 | Davidowitz | G01S 13/751 343/859 |
| 2012/0275489 A1* | 11/2012 | Lamy | G01K 7/32 374/184 |
| 2015/0016485 A1* | 1/2015 | David | F01N 11/00 374/16 |
| 2015/0102903 A1 | 4/2015 | Wilkinson | |
| 2016/0371628 A1 | 12/2016 | Wilkinson | |
| 2016/0371642 A1 | 12/2016 | Wilkinson | |
| 2016/0381438 A1 | 12/2016 | Wilkinson | |
| 2017/0018133 A1 | 1/2017 | Wilkinson | |
| 2017/0039515 A1 | 2/2017 | Wilkinson | |
| 2017/0041451 A1 | 2/2017 | Wilkinson | |

* cited by examiner

APPARATUS AND METHOD TO DETERMINE A FROZEN STATE OF AN OBJECT AS A FUNCTION OF AN RFID TAG RECEPTIONPARAMETER

RELATED APPLICATION(S)

This application claims the benefit of U.S. Provisional application No. 62/185,480, filed Jun. 26, 2015, which is incorporated by reference in its entirety herein.

TECHNICAL FIELD

These teachings relate generally to radio frequency identification tags.

BACKGROUND

Delivery receptacles are known in the art. Delivery receptacles can serve to receive unattended delivery of one or more items. The use of delivery receptacles, however, gives rise to a variety of corresponding problems. When the items being delivered are frozen or refrigerated, for example, there is a risk that the item will warm or thaw to a point of being unsuitable for its intended purpose before the recipient can recover the item from the delivery receptacle.

Refrigerated delivery receptacles can help to ameliorate such a risk. Unfortunately, refrigeration components can be a relatively expensive option that also gives rise to a variety of usage and maintenance challenges.

Radio-frequency identification (RFID) tags that include an integral, on-board temperature sensor are known in the art. Such an RFID tag could be placed inside a delivery receptacle to provide temperature readings of the interior of the delivery receptacle when read by an RFID tag reader. Though possibly a useful solution for some application settings, such RFID tags can be relatively costly and hence may not be suitable for all desired uses.

BRIEF DESCRIPTION OF THE DRAWINGS

The above needs are at least partially met through provision of the apparatus and method to determine a frozen state of an object as a function of an RFID tag reception parameter described in the following detailed description, particularly when studied in conjunction with the drawings, wherein.

Figure 1:
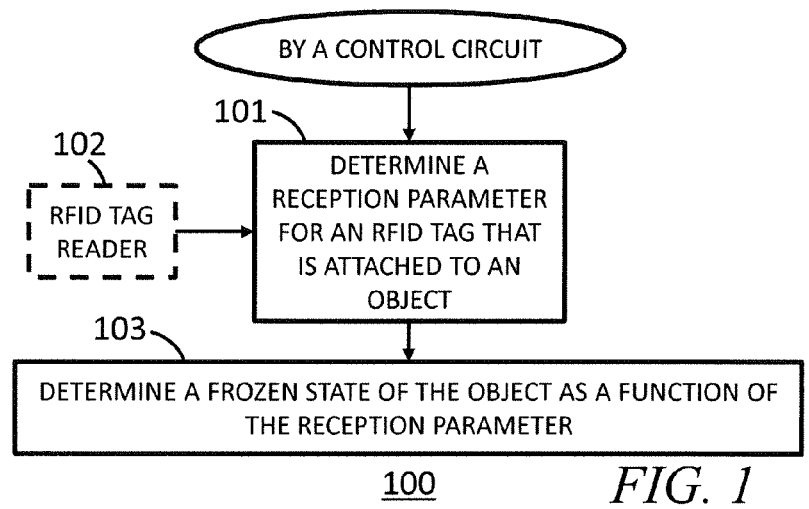
FIG. 1 comprises a flow diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit determines a reception parameter for a radio-frequency identification (RFID) tag that is attached to an object (such as an ice pack) and then determines a frozen state of the object as a function of that reception parameter. By one approach the RFID tag provides a transmission to support the aforementioned determinations that provides no data that explicitly represents temperature.

The reception parameter can comprise, for example, an indication of received signal strength. As an ice pack, for example, thaws and comprises an increasing amount of liquid, the resultant increasing quantity of liquid will absorb a corresponding increasing amount of radio-frequency energy. Accordingly, a relatively higher indication of received signal strength for the transmissions of an RFID tag can serve to determine that the object is and/or remains at least substantially frozen while a relatively lower indication of received signal strength can serve to determine that the object is not at least substantially frozen.

These teachings are highly flexible and will accommodate a variety of modifications and supplementations. As one example, the RFID tag reader that reads the RFID tag that is attached to the object to thereby glean the aforementioned reception parameter can comprise a part of a delivery container that contains the object and the RFID tag.

So configured, the frozen/not-frozen state of one or more ice blocks in a delivery container can be reliably yet inexpensively monitored to thereby better understand whether the delivered items themselves (which may be the ice blocks or which may be items that are being cooled by the ice blocks) are at risk of warming to an unwanted level. These teachings will accommodate a variety of follow-on mechanisms to leverage the resulting data including, for example, utilizing an on-board wireless transceiver to transmit alert signals that warn of unwanted warming in the delivery container.

These and other benefits may become clearer upon making a thorough review and study of the following detailed description. Referring now to the drawings, and in particular to FIG. 1, an illustrative process 100 that is compatible with many of these teachings will now be presented.

Figure 2:
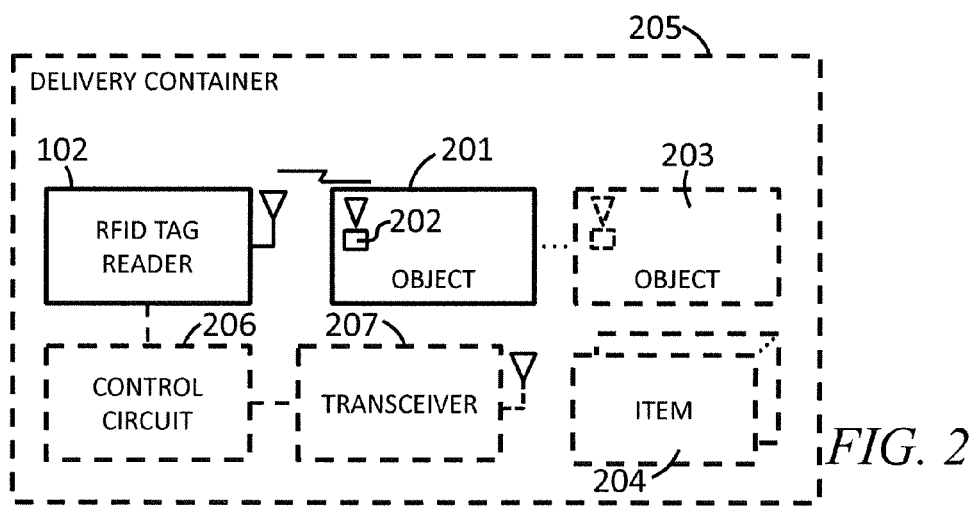
FIG. 2 comprises a block diagram as configured in accordance with various embodiments of these teachings.

For the sake of an illustrative example it will be presumed in the following description that a control circuit carries out the described process 100. Referring momentarily to FIG. 2, such a control circuit 206 can comprise a fixed-purpose hard-wired platform or can comprise a partially or wholly programmable platform. These architectural options are well known and understood in the art and require no further description here. This control circuit 206 is configured (for example, by using corresponding programming as will be well understood by those skilled in the art) to carry out one or more of the steps, actions, and/or functions described herein.

By one approach the control circuit 206 includes an integral memory (or, in lieu of the foregoing or in combination therewith, the control circuit 206 can have access to a memory that is physically discrete from the control circuit 206 as desired). This memory can serve, for example, to non-transitorily store the computer instructions that, when executed by the control circuit 206, cause the control circuit 206 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

With continued reference to both FIGS. 1 and 2, at block 101 the control circuit 206 determines a reception parameter for a radio-frequency identification (RFID) tag 202 that is attached to an object 201. In this illustrative example that object 201 comprises an ice pack. This ice pack can comprise a portable plastic sac filled with water, refrigerant gel, and/or other suitable liquid that can be frozen in a freezer. Both ice and other non-toxic (mostly water) refrigerants can absorb a considerable amount of heat before they warm above 0° C. due to the high latent heat of fusion of water.

In this illustrative example there is at least one such object 201 but there may be any number of other similar objects as denoted by reference numeral 203. It is not required that additional such objects 203 have a same size or shape as the first object 201 nor that each such object be filled with an identical liquid.

The RFID tag 202 can be attached to the object 201 by any appropriate mechanism such as, for example, a suitable adhesive. Typical prior art practice when adhering an RFID tag to a liquid-filled container calls for disposing a non-metal spacer between the RFID tag and the container. In this illustrative example, however, the use of a spacer is discouraged as a spacer can detrimentally affect the desired interaction between the RFID tag and the contents of the container per these teachings.

These teachings will accommodate using very simple and hence inexpensive RFID tags including passive RFID tags that lack many or any supplemental components such as temperature sensors. By one approach, for example, the RFID tag 202, when read by an RFID tag reader, may simply respond with its own identifier such as an identifier that is unique (at least to some extent) to that particular RFID tag. The Electronic Product Code (EPC) as managed by EPC-Global, Inc., represents one such effort in these regards. EPC-based RFID tags each have an utterly unique serial number (within the EPC system) to thereby uniquely identify each tag and, by association, each item associated on a one-for-one basis with such tags. (The corresponding document entitled EPC Radio-Frequency Identity Protocols Class-1 Generation-2 UHF RFID Protocol for Communications at 860 MHz-960 MHz Version 1.0.9 (often referred to as "EPC GEN2") is hereby fully incorporated herein by this reference.)

By one approach, the control circuit 206 determines the aforementioned reception parameter for this RFID tag 202 based upon reception data provided by an RFID tag reader 102. The reception parameter can comprise, for example, an indication of received signal strength. There are various other known ways to calculate and/or represent received signal strength (for example, the phase of the return signal and/or time delay for a response can be leveraged in these regards if desired) and the present teachings are not particularly sensitive to any specific selections in these regards. Accordingly, further elaboration regarding the measurement of received signal strength is not provided here for the sake of brevity.

By one optional approach, the aforementioned RFID tag reader 102 comprises a part of a delivery container 205 that also serves to contain the aforementioned object 201. In a typical application setting, that delivery container 205 will also likely contain one or more items 204 that are being delivered to a particular recipient or address. The ice packs comprising the object 201 in this example serve to maintain a cooled or frozen state of one or more of those items 204 pending their removal from the delivery container 205 by the recipient.

The RFID tag reader 102 can itself be programmed to read the RFID tag 202 on an automatic, periodic basis (such as once every 15 minutes, 30 minutes, 60 minutes, or other duration of interest). By another approach the aforementioned control circuit 206 can be configured to automatically prompt the RFID tag reader 102 to read the RFID tag 202 on a similar automatic, periodic basis. Upon reading the RFID tag 202 the RFID tag reader 102 can itself determine a corresponding received signal strength metric for the RFID tag's 202 response and then provide that received signal strength metric to the control circuit 206. By another approach the RFID tag reader 102 provides an unprocessed or minimally-processed version of the RFID tag's 202 response to the control circuit 206 to permit the control circuit 206 to itself ascertain the received signal strength metric.

Figure 3:
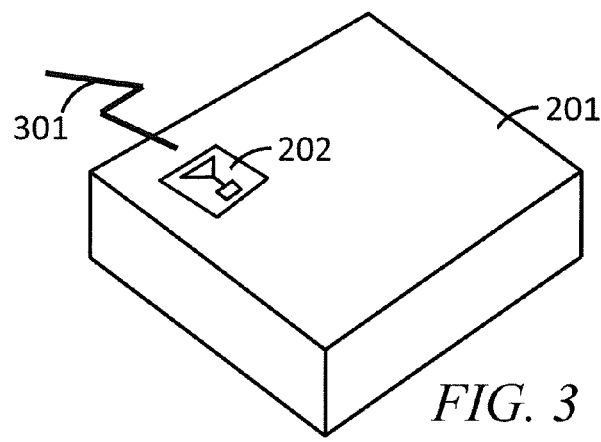
FIG. 3 comprises a perspective view as configured in accordance with various embodiments of these teachings.
Figure 4:
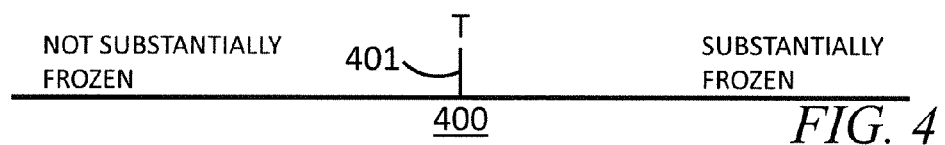
FIG. 4 comprises a graph as configured in accordance with various embodiments of these teachings.

At block 103 the control circuit 206 then determines a frozen state of the object 201 as a function of the aforementioned reception parameter (in this example, the indication of received signal strength). Generally speaking, and as illustrated in FIG. 3, the more completely frozen the object 201, the stronger the radio-frequency emissions 301 from the RFID tag 202. Accordingly, and as illustrated by the graph 400 in FIG. 4, a predetermined threshold value T 401 can serve to delineate between a substantially frozen state and a not-substantially frozen state for the object 201 based upon the amplitude of the received signal strength.

How fully the object 201 must be frozen in order to be "substantially" frozen can vary with the needs of the application setting. In some cases it may be appropriate to require that the object 201 be at least 95% frozen in order to be substantially frozen, while in other cases it may be acceptable that the object 201 be at least 90% frozen, 80% frozen, or even 75% frozen in order to be considered substantially frozen.

Figure 5:
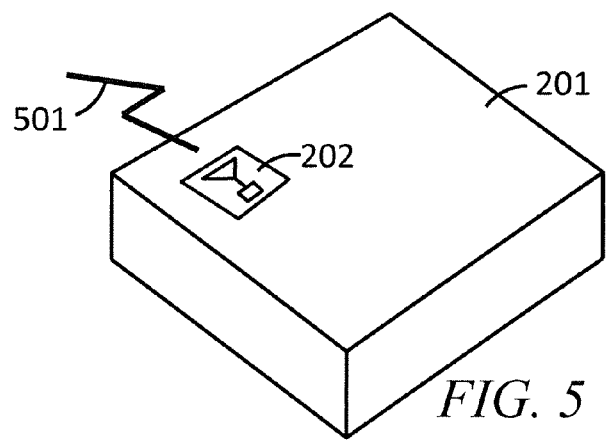
FIG. 5 comprises a perspective view as configured in accordance with various embodiments of these teachings.

As illustrated in FIG. 5, the radio-frequency emissions 501 from the RFID tag 202 will weaken as the contents of the object 201 thaw and become a radio-frequency absorbing liquid. Eventually, the thawing object 201 will harbor enough liquid that absorbs enough radio-frequency energy from the RFID tag's emissions that the corresponding received signal strength indication will be less than the aforementioned predetermined threshold T 401 and the control circuit 206 can make a corresponding determination that the frozen state of the object 201 is, for example, "not-substantially frozen."

By one approach this predetermined threshold T 401 constitutes a static, fixed value. Such an approach may be useful in situations where operating aspects of the application setting are both well-established and generally stable over time. By another approach this threshold T 401 is "predetermined" dynamically by the control circuit 206 (or, perhaps a properly-programmed RFID tag reader) at or near a time of need. Such an approach can be useful in many practical application settings where the received signal strength will be relative to a variety of dynamic factors in addition to the frozen/not-frozen state of the object 201. For example, the received signal strength can also be dependent on the orientation of the RFID tag 202 to the RFID tag reader 102. To account for such variables, these teachings will accommodate, for example, the control circuit 206 making an initial assessment of received signal strength at a time when the object 201 is known to likely be frozen completely solid and placed in a desired location in the delivery container 205. That initial assessment can serve to establish a baseline of received signal strength which the control circuit 206 can then employ to calculate the predetermined threshold T 401 for use during a particular monitoring session.

Figure 6:
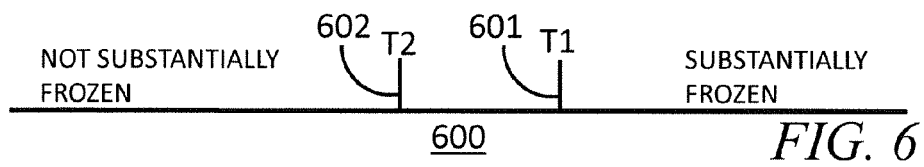
FIG. 6 comprises a graph as configured in accordance with various embodiments of these teachings.

These teachings will also accommodate using more than one threshold if desired. As illustrated by the graph 600 in FIG. 6, the control circuit 206 may employ a first threshold T1 601 to use when determining that the object 201 is substantially frozen and a second threshold T2 602 to use when determining that the object 201 is not substantially frozen. Received signal strength indications between those two thresholds T1 601 and T2 602 can serve, for example, to represent either an ambiguous frozen state for the object 201 or a cautionary state denoting that the object 201 has not yet warmed to a point of concern but is not substantially frozen either.

These teachings will accommodate any of a variety of follow-on responses to the aforementioned determinations regarding the frozen state of the object 201. By one approach the control circuit 206 simply logs those determinations (and their corresponding timestamp, if desired) for future reference and audit purposes. In lieu of the foregoing or in combination therewith, by another approach the control circuit 206 can transmit (via, for example, an available wireless transceiver 207 of choice) frozen-state information to a remote server or other authorized recipient.

By yet another approach the control circuit 206 can transmit a caution or alert when the control circuit 206 determines that the frozen state of the object 201 is insufficient (or nearing insufficiency) to maintain the desired temperature of the item 204 to be delivered. That caution/alert can assume any of a variety of forms including, if desired, text messages or emails to authorized persons such as the recipient, the delivery service, and/or the enterprise that shipped the item 204. Such information can serve to prompt a variety of responses as appropriate. By one approach, for example, the recipient can be expected to themselves take action to access the delivery container 205 in the immediate or near future and extract the item 204. By another approach the delivery service may return to the point of delivery and recover the delivery container 205.

So configured, useful temperature information can be obtained by use of simple, inexpensive RFID tags. Those RFID tags may be bereft of any dedicated temperature-sensing components and their transmissions may lack any data that explicitly represents temperature and yet these teachings permit leveraging such an RFID tag to nevertheless develop useful temperature information.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to determine a frozen state of an object, comprising:
by a control circuit:
determining a reception parameter for a radio-frequency identification (RFID) tag that is attached to the object based on radio-frequency energy emitted by the RFID tag and provided by an RFID tag reader to the control circuit, wherein the reception parameter comprises an indication of signal strength of the radio-frequency energy emitted by the RFID tag; and
determining a frozen state of the object based on the signal strength of radio-frequency energy emitted by the RFID tag;
wherein determining the frozen state of the object as a function of the reception parameter comprises, at least in part, determining that the object is at least substantially frozen when the indication of received signal strength at least equals a predetermined threshold value, wherein determining the frozen state of the object as a function of the reception parameter further comprises, at least in part, determining that the object is not at least substantially frozen when the indication of received signal strength is less than a second predetermined threshold value, and wherein the predetermined threshold value and the second predetermined threshold value each correspond to a received signal strength value, the predetermined threshold value being larger than the second predetermined threshold value.

2. The method of claim 1 wherein the signal strength is based on radio-frequency energy absorbed by the object.

3. The method of claim 1 wherein the object comprises an ice pack.

4. The method of claim 3 wherein determining the reception parameter for the RFID tag that is attached to the object comprises determining the reception parameter for the RFID tag while the ice pack is contained within a delivery container.

5. The method of claim 4 wherein determining the reception parameter for the RFID tag while the ice pack is contained within a delivery container comprises determining the reception parameter for the RFID tag using an RFID tag reader that comprises a part of the delivery container.

6. An apparatus to determine a frozen state of an object, comprising:
a radio-frequency identification (RFID) tag reader;
a control circuit operably coupled to the RFID tag reader and configured to:
determine a reception parameter for an RFID tag that is attached to the object based on radio-frequency energy emitted by the RFID tag and provided by the RFID tag reader to the control circuit, wherein the reception parameter comprises an indication of signal strength of the radio-frequency energy emitted by the RFID tag;
determine a frozen state of the object based on the signal strength of radio-frequency energy;
determine the frozen state of the object as a function of the reception parameter by, at least in part, determining that the object is at least substantially frozen when the indication of received signal strength at least equals a predetermined threshold value; and
determine the frozen state of the object as a function of the reception parameter by, at least in part, determining that the object is not at least substantially frozen when the indication of received signal strength is less than a second predetermined threshold value, wherein the predetermined threshold value and the second predetermined threshold value each correspond to a received signal strength value, the predetermined threshold value being larger than the second predetermined threshold value.

7. The apparatus of claim 6 wherein the signal strength is based on radio-frequency energy absorbed by the object.

8. The apparatus of claim 6 wherein the object comprises an ice pack, and wherein a spacer is not disposed between the RFID tag and the object.

9. The apparatus of claim 8 further comprising:
a delivery container that contains the ice pack; and
wherein the control circuit is configured to determine the reception parameter for the RFID tag that is attached to the object by determining the reception parameter for the RFID tag while the ice pack is contained within the delivery container.

10. The apparatus of claim 9 wherein the RFID tag reader comprises a part of the delivery container.

11. A method to determine a frozen state of an object, comprising:
reading a radio-frequency identification (RFID) tag that is attached to the object, wherein reading the RFID tag provides data based on signal strength of radio-frequency energy emitted by the RFID tag, wherein the data does not explicitly represents temperature;
determining a frozen state of the object based on the signal strength of radio-frequency energy;
determining the frozen state of the object as a function of reading the RFID tag comprises determining the frozen state of the object as a function of a reception parameter, wherein the reception parameter comprises an indication of signal strength of the radio-frequency energy emitted by the RFID tag;
wherein the determining the frozen state of the object as a function of the reception parameter is by, at least in part, determining that the object is at least substantially frozen when the indication of received signal strength at least equals a predetermined threshold value; and
wherein the determining the frozen state of the object as a function of the reception parameter is by, at least in part, further determining that the object is not at least substantially frozen when the indication of received signal strength is less than a second predetermined threshold value, wherein the predetermined threshold value and the second predetermined threshold value each correspond to a received signal strength value, the predetermined threshold value being larger than the second predetermined threshold value.

12. The method of claim 11 further comprising:
determining the reception parameter for the radio-frequency identification (RFID) tag while reading the RFID tag.

13. The method of claim 12, wherein the signal strength is based on radio-frequency energy absorbed by the object.

* * * * *

UNITED STATES PATENT AND TRADEMARK OFFICE
CERTIFICATE OF CORRECTION

PATENT NO. : 9,916,528 B2
APPLICATION NO. : 15/180688
DATED : March 13, 2018
INVENTOR(S) : Bruce W. Wilkinson Page 1 of 1

It is certified that error appears in the above-identified patent and that said Letters Patent is hereby corrected as shown below:

On the Title Page

Item [54], and in the Specification, Column 1, Line 4:
Delete "RECEPTIONPARAMETER" and insert --RECEPTION PARAMETER--.

Signed and Sealed this
Tenth Day of July, 2018

Andrei Iancu
*Director of the United States Patent and Trademark Office*